United States Patent [19]

Mundschenk

[11] 4,338,564

[45] Jul. 6, 1982

[54] HEMATOLOGY CONTROL COMPOSITION AND METHODS FOR ITS USE

[75] Inventor: David D. Mundschenk, Minneapolis, Minn.

[73] Assignee: R & D Systems, Inc., Minneapolis, Minn.

[21] Appl. No.: 204,238

[22] Filed: Nov. 5, 1980

Related U.S. Application Data

[62] Division of Ser. No. 47,063, Jun. 11, 1979.

[51] Int. Cl.$^3$ .............................................. G01N 27/00
[52] U.S. Cl. ............................ 324/71 CP; 235/92 PC
[58] Field of Search ............... 324/71 CP; 235/92 PC

[56] References Cited

U.S. PATENT DOCUMENTS 3,949,198 4/1976 Coulter .......................... 324/71 CP
3,963,983 6/1976 Hogg ............................. 324/71 CP

*Primary Examiner*—Michael J. Tokar
*Attorney, Agent, or Firm*—Trask & Britt

[57] ABSTRACT

A control blood platelet preparation containing a population of platelets of known count range, electronic volume and electronic volume size distribution is used to check the threshold setting calibrations of an electronic particle counter. The control preparation preferably contains blood platelets from whole blood taken from animal species which are non-infectious with respect to human hepatitis, ideally animals of the bovine and parcine species.

10 Claims, No Drawings

HEMATOLOGY CONTROL COMPOSITION AND METHODS FOR ITS USE

This is a division of application Ser. No. 047,063, filed June 11, 1979.

BACKGROUND OF THE INVENTION

1. Field

This invention pertains generally to hematology and specifically to a novel form of hematological control. It provides both a stabilized animal platelet control and a method for checking the threshold calibration of electronic particle counters.

2. State of the Art

The use of electronic particle counters in hematology is well known. U.S. Pat. No. 2,656,508 discloses a basic apparatus utilizing the Coulter principle for this purpose, U.S. Pat. No. 3,757,213 contains a description of several such devices which incorporate threshold circuitry. Threshold circuitry excludes random amplitude signals caused by noise and background debris or inconsequential particles in the suspension. It may also be used to limit the size range of particles counted. Adjustable threshold circuits with dials marked off in mathematically related dial settings are in common use. The mathematical relationship may, but need not necessarily, be linear. Coulter Electronics, Inc. of Hialeah, Florida supplies a number of publications which describe the operation of various models of electronic particle counters pertinent to this disclosure. For example, CMS catalogue No. 360-529 is an instruction manual for the Coulter Model ZBI. Coulter Electronics, Inc. also publishes an operator's reference manual for its Model S Plus (Coulter Part No. 6601221, copyrighted 1977, 1978). The disclosures of all of the foregoing patents and operators' manuals are incorporated herein by reference.

Although this disclosure will be directed primarily to embodiments involving the use of electronic particle counters of the Coulter type, it should be understood that the platelet controls herein disclosed, and their methods of use described herein, find wide application with particle counters generally. Accordingly, the term "electronic particle counter", as used herein, should be understood to include, in addition to Coulter Counters, any other type of particle counter which discriminates between particles of various sizes by the use of electronic discriminator circuits ("thresholds") which respond electronically to signals indicative of particle size, mass or other parameters related to particle volume; including those employing light scatter.

Calibration check techniques for red blood cell (erythrocytes) counts and white blood cell (leukocytes) counts are well developed. The techniques generally involve counting known populations of particles suspended in a liquid vehicle in a "control" preparation. The control preparation is usually diluted substantially (e.g., 1:3000) with a diluent prior to counting. Heretofore, however, no satisfactory platelet control for use with manual, semi-automated and automated counters has been available. Moreover, there has not heretofore evolved a reliable method and control preparation for determining the threshold factor to be applied to the control dials of threshold circuits. That is, although counts are routinely taken and reported between threshold dial values selected to fix both a lower particle size and an upper particle size for the count, the electronic volume sizes of the smallest and largest particles actually being counted are not fixed parameters on adjustable threshold particle counters. There is thus a need in the art for a reliable check of threshold calibration for electronic particle counters of the type typified by the semi-automated Coulter Counters. Operators could then identify and document the volume ranges between which platelets are to be routinely counted. There is further a need in the art for a reliable method for demonstrating instrument stability over a prolonged period of use.

SUMMARY OF THE INVENTION

According to this invention, a blood platelet control is prepared from whole blood by first treating the blood to isolate and remove the red blood cells; processing the platelets to stabilize them, that is to inhibit their surface aggregation with adjacent platelets; harvesting the platelets; and then resuspending the stabilized platelets in a plasma-like fluid which is also prepared from whole blood. The whole blood source should be non-human and non-simian; that is, it should be from a species that is non-infectious with respect to human hepatitis. Ideally the whole blood is taken from bovine or porcine species because such blood is readily available, is susceptible to processing in accordance with the techniques of this invention, and does not transmit human hepatitis. In general, the control platelet preparation of this invention is produced by collecting a quantity of whole blood; treating the blood to separate the red blood cells, leaving a liquid fraction which is rich in platelets and white cells; diluting the platelet-rich plasma (PRP) with an osmotic solution in a ratio of about 1:5 to about 1:10, so that the platelets swell until they are within the size range corresponding to human blood platelets; and then fixing the platelets to stabilize them with respect to size and resuspension during prolonged storage periods.

Typical swelling agents include hypotonic solutions of CCD, saline, urea, cocaine or any of the other agents known to the art for this purpose. According to the preferred embodiments of this invention, stabilization is halted after the proteins on the platelet membrane have cross-linked sufficiently to inhibit surface aggregation with adjacent platelets, but before the responsiveness of the platelets to external stimuli is substantially inhibited. In practice, a fixing agent ("fixative"), which may be glutaraldehyde, formaldehyde, osmium tetroxide (or other similar agent or combination of agents which cross-link plasma and membrane proteins), is added in amounts typically ranging from about 1/100 of a percent to about one percent by volume. Cross-linking is permitted to the level which will inhibit surface aggregation, leaving the platelets responsive to external stimuli as though they were fresh platelets. That is, the stabilized platelets will mimic the responses generally observed of fresh platelets to changes in diluents normally employed in counting procedures. The platelets are harvested from the resulting stabilized solution, and the remaining plasma is filtered. The filtered plasma may be used as a suspending medium (liquid vehicle) for the harvested platelets to produce the control preparations of this invention. The filtered plasma may be diluted, e.g., with normal saline, to reduce its viscosity. There results a preparation consisting of stabilized platelets (preferably animal) suspended in a plasma-like fluid. The stabilizing process and the suspending medium of the preparation maintain the platelets in their natural log-normal size distribution while allowing them to respond to changes in the diluent systems commonly used for platelet counting. The preparation is then assayed by phase contrast microscopy (or less preferably, bright light microscopy) so that the preparation is associated with a known count range. Preferably, a count is made of all platelets exceeding at least two different minimum electronic volumes. Size and size distribution are measured, employing a calibrated electronic particle counter. The preparation can then be used to accurately monitor the platelet count by diverse counting techniques, including the conventional phase or bright light microscopy, semi-automated electronic, or automated electronic techniques in current practice.

The preparations of this invention normally resuspend easily and are free from particulate aggregates. According to certain embodiments, a microtubule stabilizing agent, such as propylene glycol, is added to the preparation in an amount up to about 30 percent by volume to inhibit lysis during freezing. This addition inhibits aggregation and enhances the resuspension characteristics of the preparation.

The platelet preparations of this invention have many applications. For example, preparations of platelets as platelet-rich plasma (PRP) may be used as a platelet reference control for manual, semi-automated, and automated counting systems. A preparation of platelets may be added to conventional whole blood or red blood cell controls to provide a platelet reference control for manual, semi-automated and automated counters used for performing normal, low and abnormal low blood counts. Two different cell preparations, one of which contains a relatively high mean platelet volume and the other of which contains a relatively low mean platelet volume, may be used for threshold calibration for semi-automated electronic particle counters of the Coulter type.

The electronic particle volumes established by the threshold settings of a particle counter (of the type which includes discriminators with mathematically related dial settings to exclude particles of smaller volume than a low threshold setting) may be determined by the use of blood platelet controls of this invention. The procedure for determining electronic particle volumes is to present in counting association with the electronic particle counter a control blood platelet preparation of known electronic volume assay and of known count range for that volume. Usually, a preparation of this invention will be assayed at two particle volumes so that at least two counts are known. The discriminator means is adjusted; that is, its dial setting which produces a machine count within an acceptable error margin of the known assay is determined. The threshold factor of the discriminator is calculated by applying the mathematical relationship of the dial setting to the particle size counted at the thus-determined dial setting. The particle size; that is, the electronic volume size of both the low threshold and the upper threshold, may be determined by multiplying the dial setting value corresponding to each threshold by the threshold factor. Normal practice will be to determine the threshold factor, using a plurality of control blood platelet preparations of different volume assays, and to then compute an average threshold factor from the accumulated data.

This disclosure makes reference to a number of terms which are commonly used within the hematology art. It should be understood that such terms are used in this disclosure in harmony with their commonly accepted definitions. Unless the context clearly indicates otherwise, the following terms as used herein and in the appended claims should be understood as follows:

"electronic particle volume" means a volume determined by an electronic particle counter referenced to particles of known volume.

"true particle volume" means the physical volume of a particle or group of particles.

"volume assay" means a statistical estimate of a discrete electronic volume as determined on a calibrated particle counter.

"count assay" means the best statistical estimate of the number of particles of a particular type within a defined size range in a unit volume of sample.

"plasma-like fluid" means a liquid vehicle with viscosity and physiologic properties similar to blood plasma with respect to its interaction with platelets.

"diluent" means isotonic solution, usually buffered and containing a preservative, used for counting and sizing hematological formed elements, specifically erythrocytes and platelets.

"liquid vehicle" means plasma-like fluids or any other suspension media used for hematologic cell control preparation.

"platelet-rich plasma" means a suspension of platelets on blood plasma or plasma-like fluid from which substantially all of the erythrocytes have been removed.

"swelling reagent" means an agent in solution which causes the platelets to swell, whether by osmotic effect or by that typified by a class of compounds generally referred to as local anesthetics. The swelling is terminated by adding a "fixative".

"stabilized" refers to a condition in which the platelets in a suspension retain their size and size distribution through prolonged storage.

"CCD" refers to citrate citric acid dextrose, a standard reagent comprised of citric acid, sodium citrate and dextrose in an aqueous solution. Its usual composition per liter is 26.5 grams sodium citrate, 24.5 grams D-glucose, 1.21 grams citric acid diluted to 1 liter with distilled water. The pH is adjusted to 6.5 using 0.1 N sodium hydroxide.

"Isoton II" refers to a standard commercial diluent available from Coulter Diagnostics, Inc. of Hialeah, Florida under that trade name and is similar to other commerically available isotonic buffered saline suspensions.

DESCRIPTION OF THE PREFERRED EMBODIMENTS

The following description and examples set forth the best mode presently contemplated for carrying out the invention.

The following examples, which pertain to preparing platelet controls from whole blood of particular animal species, are generally instructive concerning the preparation of such controls from whole blood of any derivation. The examples are directed specifically to bovine and porcine whole bloods because those bloods are both readily available and are of a type preferred in practice. Specifically in each instance, bloods from the bovine and porcine species are non-infectious with respect to human hepatitis. In many instances, porcine blood is particularly preferred because the cells do not directly utilize glucose. Accordingly, the blood can be collected into a glucose medium. Although the red blood cells will crenate, they assume an approximately normal discoid configuration upon heating to about 45° C. prior to fixing.

EXAMPLE 1

Approximately one liter of porcine whole blood is mixed with approximately 200 ml of standard citrate citric acid dextrose (CCD) reagent. The mixture is allowed to settle for one hour, and is spun in conventional fashion to separate the red cells, resulting in a straw-yellow, platelet-rich plasma (PRP) supernatant. Four 100 ml aliquots of this PRP are withdrawn, and each aliquot is mixed with approximately 700 ml of dilute CCD (a hypotonic solution consisting of standard CCD diluted about five fold with distilled water). The mixtures are each warmed to approximately 37° C. for the "swelling" intervals indicated in Table 1, at which time approximately 5 ml of 25 percent glutaraldehyde is added to stabilize the platelets. The color of the liquid fraction changes from straw-yellow to dark brown. The stabilized platelet mixtures are again spun to concentrate the stabilized platelets. The resultant supernatants are withdrawn and filtered to remove debris. The liquid fractions are saved for future use as liquid vehicle for suspending the platelets. The platelets are harvested and are mixed with sufficient liquid vehicle to produce the platelet concentrations shown in Table 1.

The preparations of Example 1 consist of stabilized porcine platelets suspended in a plasma-like fluid, with electronic volumes of the platelets evidencing the approximately natural log-normal size distribution characteristic of fresh platelet populations in whole blood. The platelets are stable for prolonged storage periods of six months to one year or more, yet respond to changes in the diluent in the same fashion as the fresh platelet populations of whole blood. Each of the platelet preparations of Example 1 is assayed by phase-contrast microscopy according to the Brecker-Cronkite (1964) procedure published in *Clinical Diagnosis by Laboratory Methods,* Davidson and Henry, 15th Edition, W. W. Sanders Co., p. 125, 441. Particle counts are taken of 1:3000 Isoton II dilutions on a Model ZBI Coulter Counter using a 70 micron aperture and Isoton II diluent following the procedures recommended in the operator's manual (CMS catalogue No. 360-529) for platelet counts. Table 1 reports data and parameters pertinent to the four preparations.

TABLE 1

| Preparation Number | Swelling Interval (Minutes) | Platelet Conc. (Count/mm$^3$) | Mean Particle Vol. (fl) | Particle Dist. (GSI) |
|---|---|---|---|---|
| 1 | 7 Minutes | 2,000,000 | 13.6 | 1.60 |
| 2 | 6 Minutes | 2,500,000 | 12.5 | 1.66 |
| 3 | No Delay | 2,100,000 | 6.6 | 1.70 |
| 4 | No Delay | 2,300,000 | 6.1 | 1.72 |

| | | Numeric Assays at: Volume Assays (fl) | | | |
|---|---|---|---|---|---|
| | | A | | B | |
| Preparation Number | 95% of Platelets Vary From fl to fl | Uncorrected Count (mm$^3$) | Volume Assay (fl) | Uncorrected Count (mm$^3$) | Volume Assay (fl) |
| 1 | 4.8–31.0 | 25,000 | 11.9 | 12,000 | 18.2 |
| 2 | 4.0–30.3 | 21,500 | 12.6 | 9,100 | 20.2 |
| 3 | 2.0–16.6 | 22,000 | 5.6 | 31,000 | 3.7 |
| 4 | 1.8–15.6 | 16,100 | 7.6 | 33,500 | 3.0 |

EXAMPLE 2

Table 2 reports data and parameters pertinent to several platelet preparations from bovine blood processed and analyzed in accordance with the procedures of Example 1.

TABLE 2

| Preparation Number | Swelling Interval (Minutes) | Platelet Conc. (Count/mm$^3$) | Mean Particle Vol. (fl) | Particle Dist. (GSI) |
|---|---|---|---|---|
| 5 | 9 Minutes | 2,400,000 | 15.0 | 1.62 |
| 6 | 7.5 Minutes | 2,000,000 | 14.6 | 1.59 |
| 7 | No Delay | 2,200,000 | 6.6 | 1.61 |
| 8 | No Delay | 2,300,000 | 6.4 | 1.65 |

| | | Numeric Assays at: Volume Assays (fl) | | | |
|---|---|---|---|---|---|
| | | A | | B | |
| Preparation Number | 95% of Platelets Vary From fl to fl | Uncorrected Count (mm$^3$) | Volume Assay (fl) | Uncorrected Count (mm$^3$) | Volume Assay (fl) |
| 5 | 5.1–35.0 | 21,100 | 14.0 | 10,100 | 22.3 |
| 6 | 5.2–33.1 | 28,500 | 12.1 | 15,000 | 18.5 |
| 7 | 2.3–15.3 | 16,200 | 6.7 | 29,600 | 3.4 |
| 8 | 2.1–15.4 | 21,500 | 5.7 | 31,000 | 3.8 |

The stabilization of platelets is preferably conducted with the PRP diluted to concentrations of between about 25,000 to about 300,000 platelets per cubic millimeter (mm$^3$), preferably between about 50,000 to about 150,000/mm$^3$. The fixative is normally added in amounts below about one percent by volume, preferably less than ½ percent by volume. Sub-preparations of relatively small mean electronic volume, between about 5 and about 8 fl, and of relatively large mean electronic volume, between about 10 and about 18 fl are presently regarded as most useful. The preferred size ranges are 6 to 7.5 and 12 to 15, respectively.

EXAMPLE 3

Preparations 1 and 3 of Example 1 may be used to check the threshold calibration of any Model B, F or Z Series Coulter Counter using a 70 micron aperture. The manometer switch is set to 500 ul so that the counting time is approximately 25 seconds. The upper threshold dial of a Model Z Series instrument is turned to the "off" position. The Model B and F Series instruments have no upper threshold circuits. A sample of each preparation is mixed with Isoton II to affect a 1:3000 dilution. Accordingly, both preparations 1 and 3 possess known count and volume assays as indicated in Table 1. The dilution of preparation 1 is counted first with the low threshold dial set at 50 dial divisions. A count of 23,000 is obtained with is 2,000 lower than the numeric assay for assay point A (see Table 1). Accordingly, the dial is turned to a lower dial division and the sample is again counted. This procedure is repeated until eventually a count of 25,000 is obtained, at dial division 49. This count is considered valid because it is within plus or minus 200 of the known assay. Accordingly, the dial division and count data are entered in a table format similar to that of Table 3. The dilution of preparation 1 is next counted in the same fashion to determine the dial division for assay point B of Table 1. The dilution of preparation 3 is counted in the same way to determine the dial division for assay point A of Table 1. The dial division and count data are entered as indicated in Table 3.

TABLE 3

| Assay Points A B A | Numeric Assay Uncorrected Instrument Count | Volume Assay (fl) | Corresponding Threshold Dial Division From Coulter Counter Initial | Volume Assay (fl) / Threshold Dial Division (TDD) Step 4-1 | Threshold Factor (TF) Step 4-2 | Average Threshold Factor (AV-TF) Step 4-3 |
|---|---|---|---|---|---|---|
| A LARGE (1) | 25,000 | 11.9 | Step 2.5 (49) | $\frac{\text{Volume Assay} = (11.9)}{\text{TDD} = (49)} =$ | (0.243) | |
| B LARGE (1) | 12,000 | 18.2 | Step 2.6 (76) | $\frac{\text{Volume Assay} = (18.2)}{\text{TDD} = (76)} =$ | (0.239) | (0.242) |
| A LARGE (3) | 22,000 | 5.6 | Step 3.1 (23) | $\frac{\text{Volume Assay} = (5.6)}{\text{TDD} = (23)} =$ | (0.243) | Average Threshold Factor |

The threshold factor (TF) is calculated by dividing the volume assays from Table 3 by the corresponding threshold dial divisions. The three threshold factors are recorded in Table 3 and are averaged as shown. If the counter is linear and the aperture is clean, the three calculated threshold factors should all be within plus or minus 0.01 from the average of the three.

Table 4 illustrates a confirmation procedure for confirming the threshold factors. The dial division for assay B of preparation 3 reported in Table 1 is located following the same procedures outlined with respect to assays A and B of preparation 1 and assay A of preparation 3. The threshold dial division is recorded in Table 4 as shown. Table 4 also records the average threshold factor (the arithematic average of the three threshold factors calculated from the data of Table 3). The average threshold factor is multiplied times the dial division of assay B of preparation 3 to yield a calculated assay volume for assay point B. This calculated volume should agree with ±0.70 fl with the assay volume recorded in Table 1:

TABLE 4

| Assay Point SMALL (3) | Numeric Assay | Volume Assay (fl) | Corresponding Threshold Dial Division | Average Threshold Factor (AV-TF) × TDD | Calculated Volume (fl) |
|---|---|---|---|---|---|
| B | 31,000 | 3.7 | (15) | (.242) × (15) = | 3.6 |

The volumes representing the upper and lower threshold settings of the instrument are calculated by multiplying the normal threshold settings times the average threshold factors. The average threshold factor calculated from Table 4 is 0.241. Assuming that the lower threshold is normally set at ten dial divisions and the upper threshold is normally set at 100 divisions, the instrument is normally adjusted to count all platelets having volumes greater than 2.4 fl and less than 24.3 fl.

EXAMPLE 4

A pair of platelet controls of this invention, one of which has a relatively large mean volume and the other which has a relatively small mean volume (such as preparations 1 and 3 or 2 and 4 of Example 1) may be used to "fit check" a Coulter Model S Plus particle counter. This procedure enables the operator to periodically check and document the ability of a Model S Plus to "fit" and count abnormally large and small platelets. The Counter Counter Model S Plus (Coulter Part #6601221) is completely described in the operator's reference manual, the disclosure of which is incorporated herein by reference. It is a characteristic of that machine, that by using the X-Y recorder, the operator may graphically identify and estimate the magnitude of platelet sizes seen in abnormal patient samples. As in all of the examples of this disclosure, it is understood that conventional suspension storage and handling procedures are observed in handling the control preparations of this invention.

The fit check procedure for a Coulter Model S Plus is to first cycle a sample of large mean particle size (such as preparations 1 or 2) through the S Plus using the whole blood aspirator. An S Plus print-out card is inserted into the printer and the platelet data is plotted using the X-Y recorder, all in accordance with the instructions of the operator's manual. If the machine is operating properly, it should "fit" the raw data curve beyond 20 fl (cubic microns). The platelet count should fall within the expected range of mean values determined from statistical data obtained by replicate counts of phase contrast microscopy as previously disclosed herein. Next a sample of relatively small mean particle volume is cycled through the S Plus machine. The print-out card is inserted into the printer on the machine and data is plotted. Preparations 3 and 4 are representative of mean size volumes which approach the lower volume size limits of most S Plus fitting programs. Accordingly, results may be either "fitted" or "unfitted" (smoothed). In any event, the platelet count should fall within the expected range of mean values known for the sample preparation.

Reference herein to details of the preferred embodiment is not intended to restrict the scope of the appended claims, which themselves recite those details regarded as essential to the invention.

I claim:

1. In the method for determining the number of platelets within a size range in a selected volume of blood involving the preparation of a blood platelet sample from the blood, presenting the sample in counting association with an electronic particle counter including discriminator means having a plurality of possible threshold settings with indicia values of known mathematical relationship to each other for excluding from the count particles of smaller volume than that established by a low threshold setting, and counting the platelets in a defined quantity of said sample by means of said electronic particle counter, the improvement which comprises:

determining the electronic particle volumes established by the said threshold settings by:
presenting in counting association with said electronic particle counter a control blood platelet preparation containing a population of platelets of known count range, size and size distribution, determining the low threshold setting of said discriminator means which recognizes all platelets in said sample larger than a selected size but excludes particles smaller than that size, calculating the threshold factor of said discriminator means by applying said known mathematical relationship of the indicia values of said threshold settings to said known count of platelets so recognized by said discriminator; and determining the particle size corresponding to said possible threshold settings by multiplying the indicia value of each by the threshold factor so determined.

2. An improvement according to claim 1 wherein a plurality of control blood platelet preparations, each of which has a different volume assay, are placed in turn in counting association with said electronic particle counter; said settings of the discriminator means are determined for each control preparation; the threshold factor of the discriminator is separately calculated for each said setting; and the thresholds thus calculated are arithmetically averaged to compute an average threshold factor.

3. An improvement according to claim 2 wherein said plurality of control preparations includes at least one of relatively large mean platelet volume and at least one of relatively small mean platelet volume.

4. An improvement according to claim 2 wherein numeric assays corresponding to at least two volume assays of a control preparation having a relatively large mean particle size are established and at least one numeric assay corresponding to a volume assay of a control preparation having a relatively small mean particle size is established, the setting of said discriminator is established for each of said established numeric assays, and the average threshold factor is computed, based on said setting and said corresponding volume assays.

5. An improvement according to claim 1 wherein said control blood platelet preparation comprises platelets from blood selected from species whose blood is non-infectious with respect to human hepatitis.

6. An improvement according to claim 1 wherein said discriminator means includes an adjustable threshold circuit controlled by means having linearly related indicia values so that said threshold factor is calculated by dividing said count by the indicia value of said determined low threshold setting.

7. An improvement according to claim 6 wherein said means with linearly related indicia values is a dial, and said indicia values correspond to divisions of said dial.

8. An improvement according to claim 6 wherein a plurality of control blood platelet preparations, each of which has a different volume assay, are placed in turn in counting association with said electronic particle counter; said settings of the discriminator means are determined for each control preparation; the threshold factor of the discriminator is separately calculated for each said setting; and the thresholds thus calculated are arithmetically averaged to compute an average threshold factor.

9. An improvement according to claim 8 wherein said plurality of control preparations includes at least one of relatively large mean platelet volume and at least one of relatively small mean platelet volume.

10. An improvement according to claim 8 wherein numeric assays corresponding to at least two volume assays of a control preparation having a relatively large mean particle size are established and at least one numeric assay corresponding to a volume assay of a control preparation having a relatively small mean particle size is established, the setting of said discriminator is established for each of said established numeric assays, and the average threshold factor is computed, based on said setting and said corresponding volume assays.

* * * * *